United States Patent [19]

Bennett et al.

[11] Patent Number: 4,766,264
[45] Date of Patent: Aug. 23, 1988

[54] AROMATIZATION OF PARAFFINS

[75] Inventors: Ian C. Bennett, Weybridge; Antony H. P. Hall, Cobham, both of England

[73] Assignee: The British Petroleum Company, London, England

[21] Appl. No.: 840,385

[22] Filed: Mar. 17, 1986

[30] Foreign Application Priority Data

Mar. 27, 1985 [GB] United Kingdom ................. 8507947

[51] Int. Cl.$^4$ ............................................. C07C 12/00
[52] U.S. Cl. .................... 585/412; 585/415; 585/417; 585/418
[58] Field of Search ............... 585/407, 412, 415, 417, 585/418

[56] References Cited

U.S. PATENT DOCUMENTS

| | | | |
|---|---|---|---|
| 4,056,575 | 11/1977 | Gregory et al. | 585/407 |
| 4,260,839 | 4/1981 | Chen et al. | 585/407 |
| 4,490,569 | 12/1984 | Chu et al. | 585/407 |

FOREIGN PATENT DOCUMENTS

| | | | |
|---|---|---|---|
| 0050021 | 4/1982 | European Pat. Off. | 585/407 |
| 0147111 | 3/1985 | European Pat. Off. | 585/407 |
| 1496379 | 12/1977 | United Kingdom | 585/418 |

*Primary Examiner*—Curtis R. Davis
*Attorney, Agent, or Firm*—Brooks Haidt Haffner & Delahunty

[57] ABSTRACT

This invention relates to a process for converting a $C_2$–$C_6$ paraffin feedstock to aromatics over a gallium loaded zeolite catalyst. The feature of the invention is to bring the ethane in the feed with a fresh or freshly regenerated catalyst first and thereafter to bring the residual catalyst from this step into contact with the remainder of the $C_3$–$C_6$ feedstock. The present process has the advantage of maximizing the yields of aromatics from a mixed feedstock using a single reactor and a single charge of catalyst.

7 Claims, No Drawings

AROMATIZATION OF PARAFFINS

The present invention relates to a process for the production of aromatic hydrocarbons from a paraffinic hydrocarbon feedstock containing ethane and at least one $C_3-C_6$ paraffinic hydrocarbon.

Our prior applications describe processes for converting ethane into aromatics (EP No. 0050021) and for converting higher paraffinic hydrocarbons into aromatics (GB No. 1561590) both using a gallium loaded zeolite catalyst.

The present invention describes a method of sequentially converting two types of feedstock in a single reactor system in a specific manner.

Accordingly, the present invention is a process for the conversion of $C_2-C_6$ paraffinic hydrocarbons to aromatic hydrocarbons over a gallium loaded zeolite at elevated temperature characterised in that the process comprises the steps of:
(a) bringing a feedstock comprising predominantly ethane into contact with a freshly prepared or regenerated gallium loaded zeolite catalyst at a temperature from 550° to 650° C. over a period from 10 to 50 hours;
(b) bringing a paraffinic feedstock comprising predominantly $C_3-C_6$ hydrocarbons into contact with the residual catalyst from step (a) after contact with ethane at a temperature from 470° to 580° C. over a period from 40 to 200 hours;
(c) regenerating the residual catalyst from step (b) after contact with the $C_3-C_6$ hydrocarbon; and
(d) recycling the regenerated catalyst from step (c) to step (a).

The $C_3-C_6$ paraffinic hydrocarbon feedstock is preferably propane or a butane.

Steps (a) and (b) are both suitably carried out at a pressure in the range of 1 to 20 bar absolute using a weight hourly space velocity (WHSV) of 0.3 to 8.

The gallium loaded zeolite used in the process is suitably that which contains from 0.1 to 10% by weight of gallium, preferably from 0.2 to 5% by weight of gallium.

The zeolite on to which gallium is loaded to form the catalysts used in the present invention is an aluminosilicate which preferably has a high silica to alumina ratio, i.e. greater than 5:1. Methods of preparing such zeolites are claimed and described in our published European Patent Application Nos. 0024930 and 0030811. Zeolites of the MFI type are most preferred.

The gallium can be loaded on the zeolite from a gallium compound by ion-exchange or impregnation by well known techniques of the art, e.g. as described in our published European Patent Application No. 0050021.

The gallium loaded zeolite may be activated prior to reaction with ethane using the process described for instance in our published European Patent Application No. 0119027.

The sequential reaction is suitably carried out in a pressure swing reactor system. Alternatively a moving bed system may be used whereby fresh catalyst is fed to the first reactor and it gradually deactivates due to deposition of carbon as it passes through a series of reactors, ethane is fed to the first reactor and the $C_3-C_6$ hydrocarbons to any of the subsequent reactors.

Upon reaction with ethane in step (a), the gallium loaded catalyst is deactivated to some extent. This is due to the deposition of carbon in a concentration of e.g. 3 to 10% w/w on the catalyst in step (a). However, in spite of the deactivation of the original catalyst in step (a), the residual catalyst surprisingly retains sufficient activity to allow conversions of the higher $C_3-C_6$ paraffin hydrocarbons into aromatics at relatively lower temperatures in step (b). Moreover, in step (b) the selectivities to liquid hydrocarbons are substantially the same as those observed with a fresh catalyst.

The catalyst deactivated in step (b) may be regenerated using conventional methods, e.g. by burning off the deactivating carbon deposited thereon using air diluted with an inert gas e.g. nitrogen at elevated temperature.

The process of the present invention is further illustrated in the following Example.

EXAMPLE

The gallium loaded zeolite was prepared by a method similar to that described below. The zeolite had a silica to alumina ratio of 33:1.

A sample of an MFI-type zeolite containing ammonium cations (zeolite prepared using ammonia as template according to the general process of our published EP No. 0030811-A) was impregnated with 20 ml of an 0.04M aqueous solution of $Ga(NO_3)_3$. This solution was just sufficient to wet the zeolite. The aqueous solvent was then removed by drying at 130° C. at subatmospheric pressure.

The gallium impregnated zeolite was then bound in an inert silica matrix and sieved to give catalyst particles which passed through a standard 12 mesh sieve but were retained by a 30 mesh sieve.

This procedure gave a final catalyst containing 0.8% Ga.

Thereafter, the catalyst was modified by steam and hydrogen treatment using a procedure similar to that described in Ep-A-0119027, Example 1(1) (b).

Ethane was passed over the catalyst at 625° C. and 4.5 bar absolute with a WHSV of 1. Over a period of 24 hours an average of 37% of the ethane was converted and a 20% wt yield of aromatic liquid was obtained. The catalyst then contained 5.3% wt carbon. A mixture of propane (75% wt) and butane was then passed over the catalyst at 550° C. and 6 bar absolute with a WHSV of 2. Over 52 hours an average of 90% of the butane and 56% of the propane was converted. A 36% yield of substantially aromatic liquid was obtained.

We claim:
1. A process for the conversion of $C_2-C_6$ paraffinic hydrocarbons to aromatic hydrocarbons over a gallium loaded zeolite at elevated temperature characterised in that the process comprises the steps of:
(a) bringing a feedstock comprising predominantly ethane into contact with a freshly prepared or regenerated gallium loaded zeolite catalyst at a temperature from 550° to 650° C. over a period from 10 to 50 hours;
(b) bringing a paraffinic feedstock comprising predominantly $C_3-C_6$ hydrocarbons into contact with the residual catalyst from step (a) after contact with ethane at a temperature from 470° to 580° C. over a period from 40 to 200 hours;
(c) regenerating the residual catalyst from step (b) after contact with the $C_3-C_6$ hydrocarbon; and
(d) recycling the regenerated catalyst from step (c) to step (a).

2. A process according to claim 1 wherein the $C_3-C_6$ paraffin hydrocarbon in step (b) is propane or a butane.

3. A process according to claim 1 or 2 wherein the steps (a) and (b) are carried out at a pressure in the range of 1–20 bar absolute using a weight hourly space velocity of 0.3 to 8.

4. A process according to claim 1 or 2 wherein the gallium loaded zeolite contains from 0.1–10% by weight of gallium.

5. A process according to claim 1 or 2 wherein the sequential reaction is carried out in a pressure swing reactor system.

6. A process according to claim 1, wherein the feedstock of (a) is ethane.

7. A process according to claim 1, wherein the feedstock of (b) is a mixture of propane and butane.

* * * * *